(12) United States Patent
Yan et al.

(10) Patent No.: US 11,911,199 B2
(45) Date of Patent: Feb. 27, 2024

(54) MEDICAL IMAGING APPARATUS AND TREATMENT DEVICE

(71) Applicant: OUR UNITED CORPORATION, Xi'an (CN)

(72) Inventors: Hao Yan, Xi'an (CN); Jinsheng Li, Shenzhen (CN)

(73) Assignee: OUR UNITED CORPORATION, Xi'an (CN)

( * ) Notice: Subject to any disclaimer, the term of this patent is extended or adjusted under 35 U.S.C. 154(b) by 198 days.

(21) Appl. No.: 17/533,814

(22) Filed: Nov. 23, 2021

(65) Prior Publication Data

US 2022/0160313 A1 May 26, 2022

(30) Foreign Application Priority Data

Nov. 24, 2020 (CN) .......................... 202011334409.9
Nov. 24, 2020 (CN) .......................... 202022751836.9

(51) Int. Cl.
*A61B 6/00* (2006.01)
*G06T 11/00* (2006.01)

(52) U.S. Cl.
CPC .......... *A61B 6/4035* (2013.01); *G06T 11/005* (2013.01); *G06T 2210/41* (2013.01)

(58) Field of Classification Search
CPC ..... A61B 6/4035; A61B 6/032; A61B 6/4291; A61B 6/483; A61B 6/5258; A61B 6/5282; A61B 6/06; G06T 11/005; G06T 2210/41; G21K 1/025
See application file for complete search history.

(56) References Cited

U.S. PATENT DOCUMENTS

2014/0112431 A1* 4/2014 Mattson ................... G21K 1/10
378/146

FOREIGN PATENT DOCUMENTS

CN 100457039 2/2009

OTHER PUBLICATIONS

Yan, Hao et al., Projection correlation based view interpolation for cone beam CT: primary fluence restoration in scatter measurement with a moving beam stop array; IOP Science Publishing Physics in Medicine and Biology; Published Oct. 12, 2010, vol. 55, pp. 6353-6375.

* cited by examiner

*Primary Examiner* — Courtney D Thomas
(74) *Attorney, Agent, or Firm* — Emerson, Thomson & Bennett, LLC; Roger D. Emerson; Matt J. Wilson (57) ABSTRACT

Embodiments of the present disclosure provide a medical imaging apparatus and a treatment device. The medical imaging apparatus includes: an imaging source, a beam stop array and a detector; the beam stop array is arranged between the imaging source and the detector; and the beam stop array includes a plurality of stop elements, the plurality of stop elements are distributed in rows in a direction perpendicular to a rotation axis, and the number of the stop elements is less than or equal to a preset number. After image reconstruction is performed using the projection, shadow areas corresponding to each slice image are reduced, errors of the slice image are reduced, and the imaging quality is improved.

19 Claims, 5 Drawing Sheets

MEDICAL IMAGING APPARATUS AND TREATMENT DEVICE

CROSS-REFERENCE TO RELATED APPLICATIONS

The present disclosure claims priority to Chinese application No. 202011334409.9 filed on Nov. 24, 2020, and Chinese application No. 202022751836.9 filed on Nov. 24, 2020, which are hereby incorporated by reference in their entireties.

TECHNICAL FIELD

Embodiments of the present disclosure relate to the field of medical technology, and in particular, to a medical imaging apparatus and a treatment device.

BACKGROUND

In a medical image imaging process, because a beam emitted by an imaging source may scatter after passing through a target object, an image quality may be deteriorated. In order to overcome this problem, typically, a beam stop array (BSA) is arranged between the imaging source and the target object to block beam in a linear direction. In the process of imaging while the imaging source is blocked by the beam stop array, the scatter signals are used to perform cubic spline interpolation to estimate a scatter distribution indicative of a distribution of the scatter signals on a plane of a detector. However, there is an error in the estimation by using the cubic spline interpolation. Stop points set in the beam stop array make errors concentrate at a fixed position, which reduces imaging quality.

SUMMARY

In view of this, one of the technical problems solved by embodiments of the present disclosure is to provide a medical imaging apparatus and a treatment device for overcoming the defect that errors are concentrated in a fixed position in the prior art, which reduces imaging quality.

In a first aspect, an embodiment of the present disclosure provides a medical imaging apparatus, includes: an imaging source, a beam stop array and a detector; the beam stop array is arranged between the imaging source and the detector; and the beam stop array includes a plurality of stop elements, the plurality of stop elements are distributed in rows in a direction perpendicular to a rotation axis, and the number of the stop elements is less than or equal to a preset number.

Alternatively, in an embodiment of the present disclosure, in the beam stop array, the closer to a peripheral edge area of the beam stop array, the greater a distribution density of the stop elements.

Alternatively, in an embodiment of the present disclosure, no stop element is provided at a position of an intersection between a beam center axis of the imaging source and the beam stop array.

Alternatively, in an embodiment of the present disclosure, the number of stop elements in each row distributed in the direction perpendicular to the rotation axis is equal.

Alternatively, in an embodiment of the present disclosure, the plurality of stop elements are arranged in at least one row along a first preset direction, and an included angle greater than 0 and not equal to 90 degrees is formed between a straight line extending in the first preset direction and the rotation axis.

Alternatively, in an embodiment of the present disclosure, the number of stop elements in each row arranged along the first preset direction is equal.

Alternatively, in an embodiment of the present disclosure, the number of stop elements in each row arranged along the first preset direction is equal to the preset number.

Alternatively, in an embodiment of the present disclosure, the plurality of stop elements are arranged in at least one column along a second preset direction.

Alternatively, in an embodiment of the present disclosure, a straight line extending in the second preset direction is parallel or non-parallel to the rotation axis.

Alternatively, in an embodiment of the present disclosure, the number of stop elements in each column arranged along the second preset direction is equal.

Alternatively, in an embodiment of the present disclosure, a shape of the stop element is a cylinder or a cuboid.

Alternatively, in an embodiment of the present disclosure, the stop element is made of a material capable of stopping rays emitted by the imaging source.

Alternatively, in an embodiment of the present disclosure, the apparatus further includes a gantry, the imaging source and the detector are disposed on the gantry, to rotate around the rotation axis as the gantry rotates around the rotation axis.

Alternatively, in an embodiment of the present disclosure, the medical imaging apparatus further includes a processor, and the processor is electrically connected to the detector; the detector is configured to image when rays are blocked by the beam stop array to obtain a plurality of projections; and the processor is configured to perform interpolation estimation on the plurality of projections formed by the detector to obtain a plurality of estimated projections.

In a second aspect, an embodiment of the present disclosure provides a treatment device, including: the medical imaging apparatus as described in the first aspect or any one of the embodiments of the first aspect.

Alternatively, in an embodiment of the present disclosure, the treatment device further includes a treatment couch, and the treatment couch and a to-be-scanned object thereon are arranged between the beam stop array and the detector.

Alternatively, in an embodiment of the present disclosure, the treatment couch is configured to be able to move along an axial direction of the rotation axis when the detector is imaging, so that the plurality of stop elements are imaged in the detector, and after image reconstruction, in each slice image, the number of shadow areas formed is less than or equal to the preset number.

In the medical imaging apparatus and the treatment device provided in the embodiments of the present disclosure, the medical imaging apparatus includes an imaging source, a beam stop array and a detector; the beam stop array is arranged between the imaging source and the detector; and the beam stop array includes a plurality of stop elements, the plurality of stop elements are distributed in rows in a direction perpendicular to a rotation axis, and the number of the stop elements is less than or equal to a preset number. After image reconstruction is performed using the projections, shadow areas corresponding to each slice image are reduced, errors of the slice image are reduced, and the imaging quality is improved.

BRIEF DESCRIPTION OF THE DRAWINGS

Hereinafter, some specific embodiments of the embodiments of the present disclosure will be described in detail in an exemplary but not restrictive method with reference to the accompanying drawings. The same reference numerals in the accompanying drawings indicate the same or similar components or parts. Those skilled in the art should appreciate that these accompanying drawings are not necessarily drawn to scale. In the accompanying drawings.

DETAILED DESCRIPTION OF EMBODIMENTS

A specific implementation of embodiments of the present invention will be further described below in conjunction with the accompanying drawings of the embodiments of the present invention.

Figure 1:
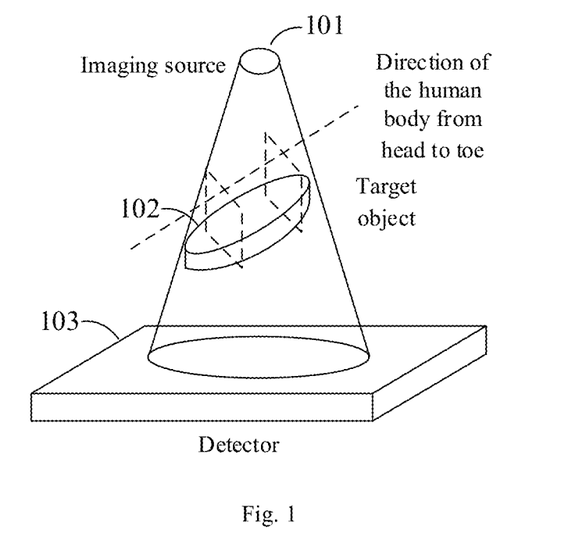
FIG. 1 is a schematic diagram of an imaging principle provided by related art.

In order to facilitate understanding, an imaging principle of the related art will be described. FIG. 1 is a schematic diagram of an imaging principle provided by related art. FIG. 1 shows an imaging source 101, a target object 102 and a detector 103. Rays emitted by the imaging source 101 pass through the target object 102 and are received by the detector 103. The target object 102 may be a part or all of a human body. Using the target object being the human body as an example, because tissues in the human body have different absorption rates of rays, after the rays pass through the human body, different areas of the detector receive different ray energy, so as to form projections. Specifically, after the rays pass through the human body, they are received by detection units on the detector, and one detection unit may correspond to one image unit (for example, one pixel). Performing image reconstruction on a plurality of projections to obtain a plurality of slice images shows an inside of the human body. Exemplarily, the plurality of slice images may be obtained in a direction perpendicular to the human body from head to toe, that is, a plane shown by a slice image is perpendicular to the direction of the human body from head to toe. As shown in FIG. 1, one slice image may show a transverse plane of the human body. In the above imaging process, the rays may scatter after passing through the human body, that is, deviate from the direction in which the rays are emitted from the imaging source, which may deteriorate the image quality.

Figure 2:
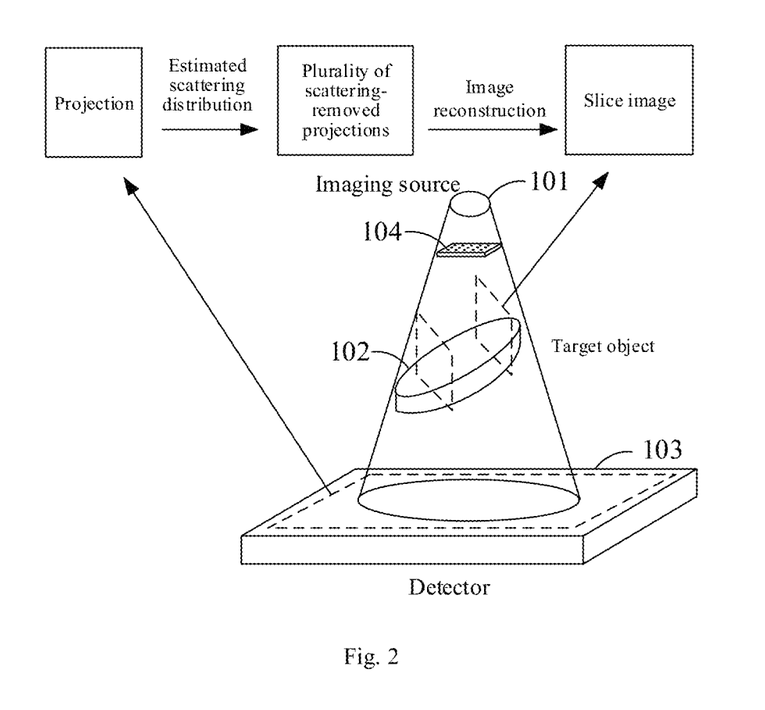
FIG. 2 is a schematic diagram of another imaging principle provided by related art.

In order to overcome this problem, a beam stop array 104 may be arranged between the imaging source and the target object. FIG. 2 is a schematic diagram of another imaging principle provided by related art. The beam stop array 104 may be an array of lead points. The lead points may block the rays emitted by the imaging source. When the beam stop array 104 blocks the imaging source for imaging, since rays irradiated on the lead points are blocked, signals of corresponding shadow areas at the lead points are all formed by scattered rays. Since the scatter signals are low-frequency (slowly or smoothly changing), a relatively small number of sampling points are collected, and the scatter signals are used to perform cubic spline interpolation to estimate a scatter distribution, then the scatter signals are removed from projection to obtain an estimated projection after the scatter distribution is estimated. Because part of the scatter signals within the shadow area in the projection are obtained by estimation, there will be some error, and when a plurality of projections in which the scatter signals are removed are used for image reconstruction to obtain the slice images, there will be errors in the position corresponding to the shadow areas of the slice images. Based on the slice images formed by the beam stop array (A*B lead points (A and B represent numbers)) shown in FIG. 2, there may be errors in the corresponding position of the lead points (i.e., the position of B lead points) on each slice image, the position of errors on each slice image (that is, the shadow areas corresponding to the lead points) is the same, moreover, concentrated in A slice images, and other slice images have no error, and the quality of those A slice images is poor.

Figure 3:
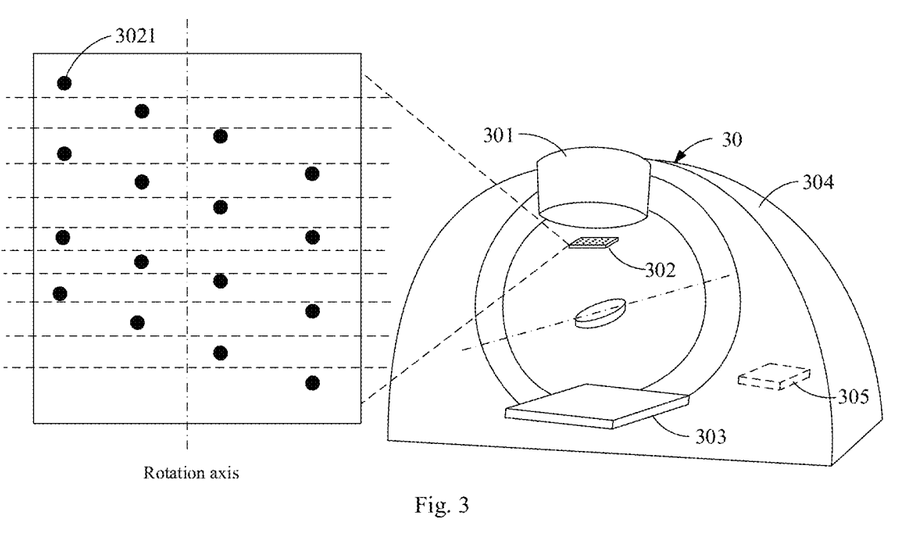
FIG. 3 is a structural diagram of a medical imaging apparatus provided by an embodiment of the present disclosure.

To solve the above problem, an embodiment of the present disclosure provides a medical imaging apparatus. FIG. 3 is a structural diagram of a medical imaging apparatus provided by an embodiment of the present disclosure. The medical imaging apparatus 30 includes: an imaging source 301, a beam stop array 302, and a detector 303; the beam stop array 302 is arranged between the imaging source 301 and the detector 303; the beam stop array 302 includes a plurality of stop elements 3021, the plurality of stop elements 3021 are distributed in rows in a direction perpendicular to a rotation axis, and the number of the stop elements 3021 is less than or equal to a preset number.

It should be noted that the stop elements 3021 may block the rays emitted by the imaging source 301. Alternatively, in an embodiment of the present disclosure, the stop element 3021 is made of a material capable of stopping rays emitted by the imaging source 301, and the material of the stop element 3021 may be a material having a high atomic coefficient, and a stop effect is good. For example, the stop element 3021 may be lead, tungsten, or other high atomic number material. A shape of the stop element may be a cylindrical structure, for example, a cylinder or a cuboid. The preset number may be an integer such as 5, 4, 3, 2, or 1, which is not limited in the present disclosure. The rotation axis may be a rotation axis of the imaging apparatus. Alternatively, in another embodiment of the present disclosure, the imaging apparatus further includes a gantry 304. The imaging source 301 and the detector 303 are arranged on the gantry 304, to rotate around the rotation axis as the gantry 304 rotates around the rotation axis. A line connecting a center of the imaging source 301 and a center of the detector 303 intersects a rotation axis of the gantry 304. The detector 303 includes a detection array composed of a plurality of detection points.

In one or more embodiments of the present disclosure, when the beam stop array 302 blocks the rays emitted by the imaging source 301 at a plurality of different angles, the detector 303 performs imaging to obtain a plurality of projections corresponding to the angles. Each of the plurality of projections includes a plurality of projection data, and each projection data corresponds to a detection point of the detection array of the detector 303 respectively. For each projection, the scatter distribution in the projection is estimated, and the estimated scatter signals are removed. The plurality of projections in which the scatter signals are removed are used for image reconstruction to obtain a plurality of slice images. A slice image may be an image representing a transverse plane of the target object, and the transverse plane represented by the slice image is perpendicular to the rotation axis. Alternatively, in another embodiment of the present disclosure, in each slice image, the number of shadow areas formed corresponding to the shadow areas of the stop elements is less than or equal to the preset number. Because the number of shadow areas corresponding to the beam stop array 302 in a slice image is less than or equal to the preset number, an error distribution in each slice image is reduced, and an overall imaging quality is improved. It should also be noted that the imaging source 301 is used to emit imaging beams; the beam stop array 302 may be arranged below the imaging source 301, and the number of rows of stop elements 3021 distributed in the direction perpendicular to the rotation axis of the beam stop array 302 may be greater than a first preset number of rows; and the detector 303 may acquire beams passing through the beam stop array 302 and generate projections. The number of rows of shadows corresponding to the stop elements 302 distributed in the direction perpendicular to the rotation axis in the projections is greater than a second preset number of rows. As shown in FIG. 2, the first preset number of rows may be A, and the first preset number of rows may be equal to the second preset number of rows. Compared with the beam stop array shown in FIG. 2, the number of stop elements 3021 is not reduced, ensuring the accuracy of the interpolation estimation. By increasing the number of rows, the number of stop elements 3021 per row may be reduced, thereby reducing the number of shadow areas corresponding to the beam stop array 302 in a slice image, and reducing the error distribution in each slice image, improving the overall imaging quality.

Figure 4:
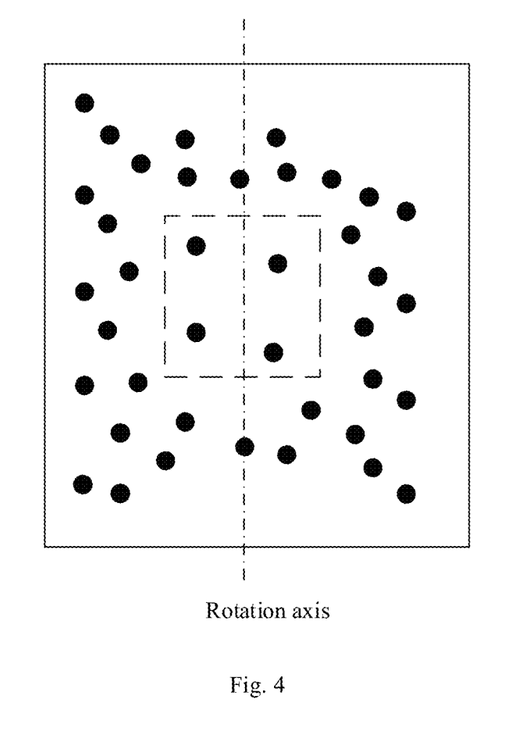
FIG. 4 is a schematic diagram of a beam stop array provided by an embodiment of the present disclosure.

The stop elements 3021 may be distributed in a plurality of ways. For example, in an implementation, the number of stop elements in each row distributed in the direction perpendicular to the rotation axis is equal. As another example, in another implementation, the plurality of stop elements 3021 included in the beam stop array 302 are randomly distributed. The plurality of stop elements 3021 are randomly distributed, so that shadow area errors formed by the stop elements 3021 are randomly distributed in the plurality of slice images. Here, two specific application scenarios are listed for description:

In a first application scenario, FIG. 4 is a schematic diagram of a beam stop array 302 provided by an embodiment of the present disclosure. Alternatively, in an embodiment of the present disclosure, stop elements 3021 of different densities are provided in different areas, and areas with stop elements 3021 of high density form more shadow areas in the area corresponding to the slice image, and the image quality is poor. In areas with stop elements 3021 of low density, there are fewer shadow areas formed in the area corresponding to a first projection, and the image quality is high. By setting different densities of stop elements 3021 in different areas, errors may be concentrated in specific areas. Stop elements 3021 in a center area of the beam stop array 302 may have a lower distribution density than stop elements 3021 in other areas of the beam stop array 302. For example, in an embodiment of the present disclosure, no stop element 3021 is provided at a position of an intersection between a beam center axis of the imaging source and the beam stop array 302. Because the center area corresponding to the beam stop array 302 is usually a key area for imaging observation, no stop element 3021 is provided at the position of the intersection between the beam center axis of the imaging source and the beam stop array 302, so that the center area is not blocked by shadows, which improves the imaging quality of the key area.

Further and alternatively, in an embodiment of the present disclosure, in the beam stop array 302, the closer to a peripheral edge area of the beam stop array 302, the greater a distribution density of the stop elements 3021. Because a center area of the target object usually contains a to-be-observed object, the distribution density of the stop elements 3021 in the center area of the beam stop array 302 is low, which may reduce the corresponding shadow areas formed by a center area of the first projection, so that a slice image corresponding to the center area has small error and higher quality, which ensures that the image of the to-be-observed object has small errors and higher quality.

In a second application scenario, the stop elements 3021 may be arranged in rows and columns. For example, the plurality of stop elements 3021 are arranged in at least one row along a first preset direction, and an included angle greater than 0 and not equal to 90 degrees is formed between a straight line extending in the first preset direction and the rotation axis. In an embodiment of the present disclosure, the number of stop elements 3021 in each row arranged along the first preset direction may be equal. Further, the number of stop elements 3021 in each row arranged along the first preset direction is equal to the preset number. Of course, this is only an exemplary description, and the number of stop elements 3021 in each row arranged along the first preset direction may also be other values, which is not limited in the present disclosure. As another example, in another embodiment of the present disclosure, the plurality of stop elements 3021 are arranged in at least one column along a second preset direction. Further, the number of stop elements 3021 in each column arranged along the second preset direction is equal. It should be noted that a straight line extending in the second preset direction is parallel or non-parallel to the rotation axis, and the first preset direction and the second preset direction are different.

Figure 5:
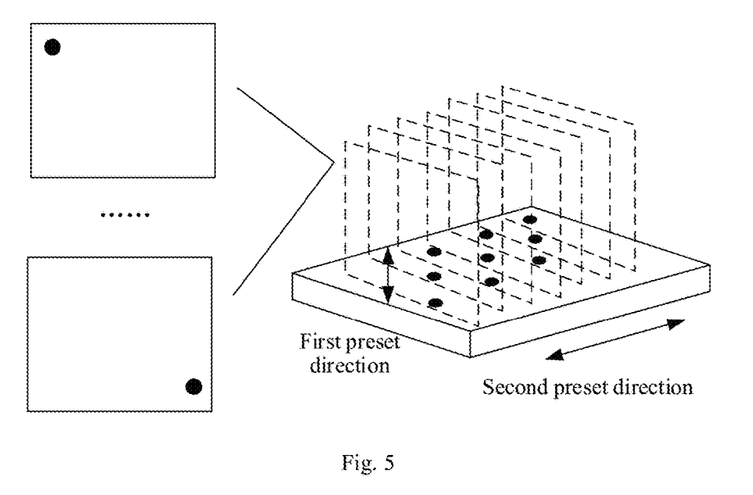
FIG. 5 is a schematic diagram of an imaging effect provided by an embodiment of the present disclosure.

Based on the second application scenario, FIG. 5 is a schematic diagram of an imaging effect provided by an embodiment of the present disclosure. Because an included angle greater than 0 and not equal to 90 degrees is formed between the straight line in which a row of stop elements 3021 arranged along the first preset direction are disposed (that is, the straight line extending in the first preset direction) and the rotation axis, and the plane of the slice of the target object is perpendicular to the rotation axis, therefore, when forming the slice image, a slice image may only include a shadow area corresponding to one stop element 3021, and the shadow area is evenly distributed on a plurality of slice images, and the shadow area on each slice image is reduced, which improves the quality of the slice image, so that the slice image can more accurately reflect the condition of the target object.

Figure 6:
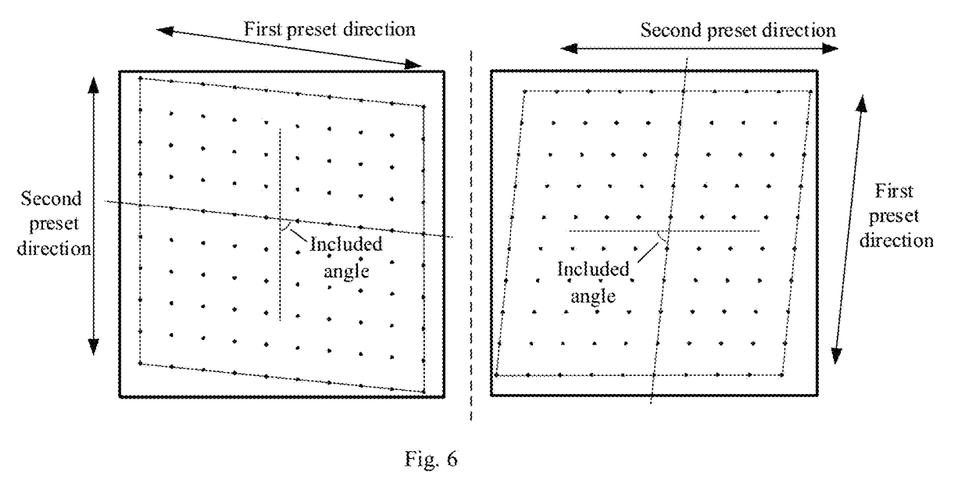
FIG. 6 is a schematic diagram of a beam stop array provided by an embodiment of the present disclosure.

Here, a specific example is given to describe in detail the distribution of the stop elements 3021 in the beam stop array 302 in the second application scenario, as shown in FIG. 6, FIG. 6 is a schematic diagram of a beam stop array 302 provided by an embodiment of the present disclosure. The beam stop array 302 includes a plurality of stop elements 3021 arranged in rows along the first preset direction and arranged in columns along the second preset direction to form m rows and n columns, and an included angle greater than 0 and not equal to 90 degrees is formed between the straight line in which a row of stop elements 3021 arranged along the first preset direction are disposed and the straight line in which a column of stop elements 3021 arranged along the second preset direction are disposed, and m and n are integers greater than 1. It should be noted that the included angle may be 80 degrees or 70 degrees, etc., which is not limited in the present disclosure. FIG. 6 shows the beam stop array 302 and the distribution of the beam stop array 302 after being rotated by 90 degrees. The present disclosure describes the distribution of the stop elements 3021 in the beam stop array 302 based on an angle, and other beam blocking arrays 302 that rotate and transform the beam blocking array 302 to achieve the same purpose are all within the protection scope of the present disclosure. It should be noted that a profile of the beam stop array 302 is a parallelogram. Alternatively, the profile of the beam stop array 302 may be a diamond shape.

Figure 7:
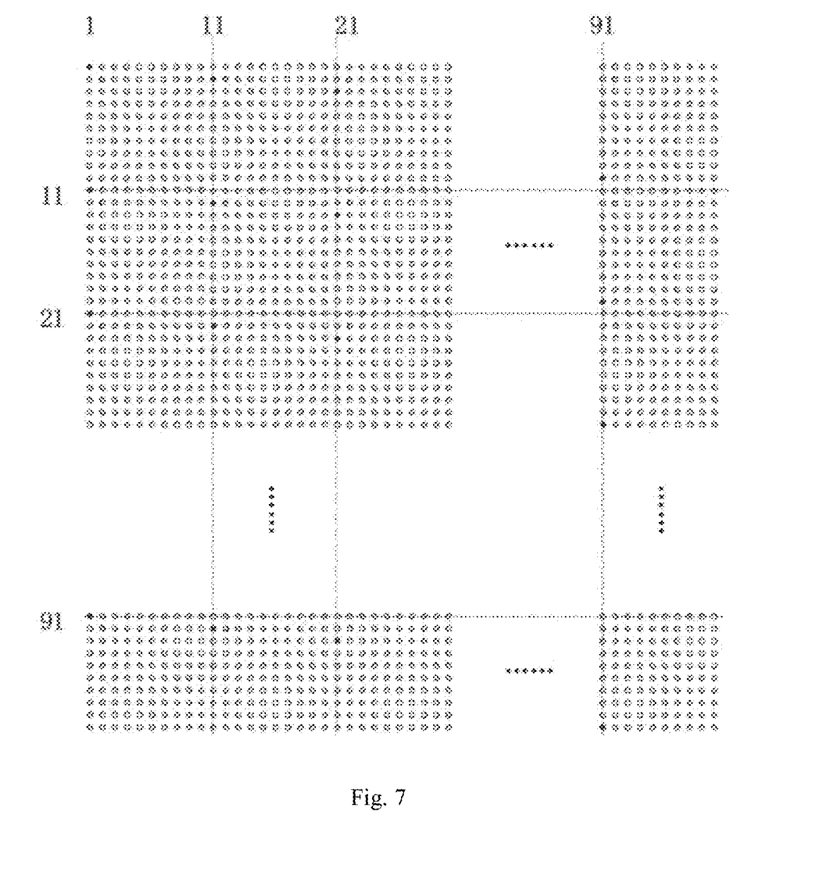
FIG. 7 is a schematic diagram of a medical image provided by an embodiment of the present disclosure.

Of course, the above is only an exemplary description, and does not mean that the present disclosure is limited thereto. In combination with the beam stop array 302 shown in FIG. 6, FIG. 7 is a schematic diagram of a medical image provided by an embodiment of the present disclosure. Taking the beam stop array 302 including 10*10 stop elements 3021 as an example, for a detector 303 with a pixel number of 100*100, there may be an array shadow (black dot) every 9 arrays. Specifically, as shown in FIG. 7, in the first column, starting from the first array, a shadow may be formed every 9 arrays; in the $11^{th}$ column, starting from the second array, a shadow may be formed every 9 arrays; in the $21^{st}$ column, starting from the third array, a shadow may be formed every 9 arrays, and so on, in the $91^{st}$ column, starting from the $10^{th}$ array, a shadow may be formed every 9 arrays. In this way, the errors may be evenly distributed in each slice image distributed along the direction of the rotation axis, the scatter is effectively corrected, and the imaging quality is high. At the same time, because the beam stop array 302 blocks a part of the rays, a radiation dose irradiated to the target object is relatively reduced, and low-dose imaging is realized. It should be noted that the above example is described by taking one stop element 3021 blocking one pixel as an example. In the present disclosure, one stop element 3021 may block one image unit, and one image unit may include one or more pixels.

Based on the above description, alternatively, as shown in FIG. 3, in an embodiment of the present disclosure, the medical imaging apparatus 30 further includes a processor 305, and the processor 305 is electrically connected to the detector 303; the detector 303 is configured to image when rays are blocked by the beam stop array 302 to obtain a plurality of projections; and the processor 305 is configured to perform interpolation estimation on the plurality of projections formed by the detector 303 to obtain a plurality of estimated projections. Further, image reconstruction may be performed on the plurality of estimated projections, and a plurality of slice images of the target object may be obtained. Specifically, the scatter signals in the shadow may be used to perform cubic spline interpolation to estimate an overall scatter distribution.

Of course, the steps performed by the processor 305 may also be completed on another device. For example, the medical imaging apparatus 30 transmits a plurality of projections to another device, and the other device performs interpolation estimation on the plurality of projections, and then uses the estimated plurality of projections to perform image reconstruction to obtain a plurality of slice images. Of course, this is only an exemplary description, which does not mean that the present disclosure is limited thereto.

It should be noted that the first projection may be estimated by using a cubic spline difference algorithm or an artificial intelligence model, which is not limited in the present disclosure.

In the medical imaging apparatus provided in the embodiments of the present disclosure, the medical imaging apparatus includes an imaging source, a beam stop array, a detector and a gantry; the beam stop array is arranged between the imaging source and the detector; and the beam stop array includes a plurality of stop elements, the plurality of stop elements are distributed in rows in a direction perpendicular to a rotation axis, and the number of the stop elements is less than or equal to a preset number. After image reconstruction is performed using the projection, shadow areas corresponding to each slice image are reduced, errors of the slice image are reduced, and the imaging quality is improved.

Figure 8:
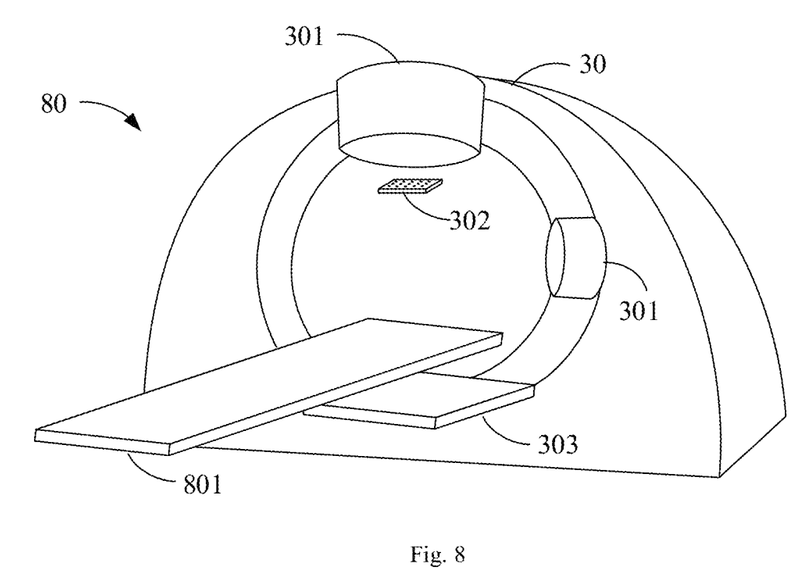
FIG. 8 is a structural diagram of a treatment device provided by an embodiment of the present disclosure.

Based on the medical imaging apparatus described in the above embodiments, an embodiment of the present disclosure provides a treatment device. As shown in FIG. 8, the treatment device 80 includes the medical imaging apparatus 30 described in any one of the embodiments of the present disclosure. It should be noted that the number of imaging sources 301 may be multiple. Two imaging sources 301 are shown in FIG. 8, which are merely exemplary, and do not mean that the present disclosure is limited thereto.

Alternatively, in an embodiment of the present disclosure, the treatment device 80 further includes a treatment couch 801, and the treatment couch 801 and a to-be-scanned object thereon are arranged between the beam stop array 302 and the detector 303.

Alternatively, in an embodiment of the present disclosure, the treatment couch is configured to be able to move along an axial direction of the rotation axis when the detector is imaging, so that the plurality of stop elements are imaged in the detector, and after image reconstruction, in each slice image, the number of shadow areas formed is less than or equal to the preset number. In combination with the process of imaging a projection described in the above embodiments, in the present embodiment, the treatment couch may be moved when imaging the projection to acquire a larger range of projection.

In the treatment device provided in the embodiment of the present disclosure, the beam stop array includes a plurality of stop elements, the plurality of stop elements are distributed in rows in a direction perpendicular to a rotation axis, and the number of the stop elements is less than or equal to a preset number, so that after image reconstruction is performed using the projection, shadow areas corresponding to each slice image are reduced, errors of the slice image are reduced, and the imaging quality is improved.

It should also be noted that the terms "including," "comprising," or any other variation thereof are intended to encompass non-exclusive inclusion, such that a process, method, product, or device that includes a series of elements includes not only those elements but also other elements not explicitly listed, or those that are inherent to such process, method, product, or device. Without more restrictions, elements defined by the sentence "including a . . . " do not exclude the existence of other identical elements in the process, method, product or device including the said elements.

The embodiments in this specification are described in a progressive method, and the same or similar parts between the embodiments may refer to each other. Each embodiment focuses on the differences from other embodiments. In particular, for the system embodiment, since it is basically similar to the method embodiment, the description thereof is relatively simple. For related details, reference may be made to the part of description in the method embodiment.

The above description is merely embodiments of the present disclosure and is not intended to limit the present disclosure. For those skilled in the art, the present disclosure may have various modifications and changes. Any modification, equivalent replacement, improvement, etc. made within the spirit and principle of the present disclosure shall be included in the scope of the claims of the present disclosure.

What is claimed is:

1. A medical imaging apparatus, comprising: an imaging source, a beam stop array and a detector; wherein,
the beam stop array is arranged between the imaging source and the detector, the imaging source and the detector are disposed on a gantry, to rotate around a rotation axis as the gantry rotates around the rotation axis; and
the beam stop array includes a plurality of stop elements, the plurality of stop elements are distributed in rows in a direction perpendicular to the rotation axis, and a number of the stop elements in each row is less than a preset number, the preset number being a number of intersections of straight lines passing through the plurality of stop elements in a direction of the rotation axis with a plane perpendicular to the rotation axis;
wherein the medical imaging apparatus further comprises a processor, and the processor is electrically connected to the detector;
the detector is configured to image when rays are blocked by the beam stop array to obtain a plurality of projections, each of the projections comprises a plurality of shadow area corresponding to the plurality of stop elements;
the processor is configured to estimate a scattering distribution in the projections, remove estimated scattering in the projections, and use a plurality of projections with the estimated scattering removed for image reconstruction to obtain a plurality of slice images, wherein a plurality of shadow areas corresponding to the plurality of stop elements are distributed in the plurality of slice images, and a number of the shadow areas in each slice image is less than the preset number.

2. The medical imaging apparatus according to claim 1, wherein in the beam stop array, the closer to a peripheral edge area of the beam stop array, the greater a distribution density of the stop elements.

3. The medical imaging apparatus according to claim 2, wherein no stop element is provided at a position of an intersection between a beam center axis of the imaging source and the beam stop array.

4. The medical imaging apparatus according to claim 1, wherein a number of the stop elements in each row distributed in the direction perpendicular to the rotation axis is equal.

5. The medical imaging apparatus according to claim 1, wherein the plurality of stop elements are arranged in at least one row along a first preset direction, and an included angle greater than 0 and not equal to 90 degrees is formed between a straight line extending in the first preset direction and the rotation axis.

6. The medical imaging apparatus according to claim 5, wherein a number of the stop elements in each row arranged along the first preset direction is equal.

7. The medical imaging apparatus according to claim 6, wherein the number of the stop elements in each row arranged along the first preset direction is equal to the preset number.

8. The medical imaging apparatus according to claim 5, wherein the plurality of stop elements are arranged in at least one column along a second preset direction.

9. The medical imaging apparatus according to claim 8, wherein the straight line extending in the second preset direction is parallel or non-parallel to the rotation axis.

10. The medical imaging apparatus according to claim 8, wherein a number of the stop elements in each column arranged along the second preset direction is equal.

11. The medical imaging apparatus according to claim 1, wherein a shape of the stop element is a cylinder or a cuboid.

12. The medical imaging apparatus according to claim 1, wherein,
the stop element is made of a material capable of stopping rays emitted by the imaging source.

13. The medical imaging apparatus according to claim 1, wherein
the processor is configured to perform interpolation estimation on the plurality of projections formed by the detector to obtain a plurality of estimated projections.

14. A treatment device, comprising: the medical imaging apparatus according to claim 1.

15. The treatment device according to claim 14, wherein,
the treatment device further comprises a treatment couch, and the treatment couch and a to-be-scanned object thereon are arranged between the beam stop array and the detector.

16. The treatment device according to claim 15, wherein,
the treatment couch is configured to be movable along an axial direction of the rotation axis when an imaging is performed by the detector, so that the plurality of stop elements are imaged in the detector, and a number of shadow areas formed in each slice image after image reconstruction is less than or equal to the preset number.

17. The treatment device according to claim 14, wherein in the beam stop array, the closer to a peripheral edge area of the beam stop array, the greater a distribution density of the stop elements.

18. The treatment device according to claim 14, wherein no stop element is provided at a position of an intersection between a beam center axis of the imaging source and the beam stop array.

19. The treatment device according to claim 14, wherein the stop element is made of a material capable of stopping rays emitted by the imaging source.

* * * * *